(12) United States Patent
Oste et al.

(10) Patent No.: US 10,750,771 B2
(45) Date of Patent: Aug. 25, 2020

(54) FOOD SUPPLEMENT COMPRISING AMINO ACID AND CHROMIUM

(75) Inventors: Rickard Oste, Lund (SE); Elin Ostman, Kavlinge (SE); Inger Bjorck, Billinge (SE)

(73) Assignee: INNOVAFOOD AB, Flyinge (SE)

(*) Notice: Subject to any disclaimer, the term of this patent is extended or adjusted under 35 U.S.C. 154(b) by 0 days.

(21) Appl. No.: 14/128,739

(22) PCT Filed: Jun. 20, 2012

(86) PCT No.: PCT/SE2012/050686
§ 371 (c)(1),
(2), (4) Date: Dec. 23, 2013

(87) PCT Pub. No.: WO2012/177215
PCT Pub. Date: Dec. 27, 2012

(65) Prior Publication Data
US 2014/0154355 A1    Jun. 5, 2014

(30) Foreign Application Priority Data
Jun. 23, 2011 (SE) ...................................... 1150583

(51) Int. Cl.
*A23L 33/175* (2016.01)
*A61K 31/198* (2006.01)
(Continued)

(52) U.S. Cl.
CPC .............. *A23L 33/175* (2016.08); *A23L 33/16* (2016.08); *A23L 33/18* (2016.08); *A61K 31/185* (2013.01); *A61K 31/198* (2013.01); *A61K 31/375* (2013.01); *A61K 31/405* (2013.01); *A61K 33/06* (2013.01); *A61K 33/24* (2013.01); *A61K 38/011* (2013.01); *A61K 38/014* (2013.01); *A61K 38/017* (2013.01); *A61K 38/018* (2013.01); *A61K 38/03* (2013.01)

(58) Field of Classification Search
CPC ........ A23L 1/304; A23L 1/3051; A23K 38/03
See application file for complete search history.

(56) References Cited

U.S. PATENT DOCUMENTS

| | | |
|---|---|---|
| 5,132,113 A | 7/1992 | Luca |
| 5,614,224 A | 3/1997 | Womack |

(Continued)

FOREIGN PATENT DOCUMENTS

| | | |
|---|---|---|
| CN | 101019888 A | 8/2007 |
| CN | 101180048 A | 5/2008 |

(Continued)

OTHER PUBLICATIONS

Kelly, G.S., "Insulin resistance: lifestyle and nutritional interventions"—Alternative Medicine Review: a Journal of Clinical Therapeutic, 2000, 5(2), Abstract only.*

(Continued)

*Primary Examiner* — Elizabeth Gwartney
(74) *Attorney, Agent, or Firm* — Christopher & Weisberg, P.A.

(57) ABSTRACT

Disclosed is a food supplement including at least the amino acids leucine, isoleucine, valine, threonine and lysine and Chromium. Also disclosed are food compositions including the food supplement as well as uses of both.

8 Claims, 1 Drawing Sheet

(51) Int. Cl.

| | |
|---|---|
| *A61K 31/185* | (2006.01) |
| *A61K 31/405* | (2006.01) |
| *A61K 33/06* | (2006.01) |
| *A61K 31/375* | (2006.01) |
| *A61K 33/24* | (2019.01) |
| *A61K 38/03* | (2006.01) |
| *A61K 38/01* | (2006.01) |
| *A23L 33/18* | (2016.01) |
| *A23L 33/16* | (2016.01) |

(56) References Cited

U.S. PATENT DOCUMENTS

| | | | |
|---|---|---|---|
| 5,719,133 | A | 2/1998 | Schmidl et al. |
| 5,925,377 | A | 7/1999 | Gerth et al. |
| 2004/0219188 | A1 | 11/2004 | Comer et al. |
| 2005/0113287 | A1 | 5/2005 | Nelson |
| 2010/0003368 | A1* | 1/2010 | Kerr .................. A23K 10/16 426/61 |

FOREIGN PATENT DOCUMENTS

| | | |
|---|---|---|
| CN | 101420867 A | 4/2009 |
| CN | 101657106 A | 2/2010 |
| DE | 10221403 A1 | 12/2003 |
| EP | 0259167 A2 | 3/1988 |
| EP | 1 680 967 | 7/2006 |
| EP | 1680967 A1 | 7/2006 |
| JP | H04-95026 A | 3/1992 |
| JP | H04-346770 A | 12/1992 |
| JP | 2000-119179 A | 4/2000 |
| JP | 2005-536215 A | 12/2005 |
| JP | 2009-536016 A | 10/2009 |
| WO | 9401006 A2 | 7/1993 |
| WO | 2004/017764 A1 | 3/2004 |
| WO | 2005/099483 | 10/2005 |
| WO | 2006060578 A2 | 6/2006 |
| WO | 2006/102451 A2 | 9/2006 |
| WO | 2007/049818 | 5/2007 |
| WO | 2007/049818 A1 | 5/2007 |
| WO | 2007049818 A1 | 5/2007 |
| WO | 2007/084059 | 7/2007 |
| WO | 2007/084059 A1 | 7/2007 |
| WO | 2007/116091 A1 | 10/2007 |
| WO | 2008028951 A1 | 3/2008 |
| WO | 2008/103179 A1 | 8/2008 |
| WO | 2010/132774 A1 | 11/2010 |

OTHER PUBLICATIONS

Chang et al., "Effect of function yogurt NY-YP901 in improving the trait of metabolic syndrome"—European Journal of Clinical Nutrition (2011) 65, pp. 1250-1255.*

International Search Report dated Sep. 20, 2012, corresponding to PCT/SE2012/050686.

Anderson, Richard, "Chromium and insulin resistance", Nutrition Research Reviews, 2003, vol. 16, pp. 267-275.

Australian Examination Report, dated May 20, 2015, from corresponding Australian Application No. 2012273516.

Chinese Examination Report, dated Feb. 2, 2015, from corresponding Chinese Application No. 201280036279.8.

Japanese Examination Report, dated Mar. 22, 2016, from corresponding Japanese Application No. 2014-516953.

Cocho, Jose-Angel, et al., "Chromium Content in Human Milk, Cow's Milk, and Infant Formulas," Biological Trace Element Research, 1992, vol. 32, pp. 105-107.

"Nutrient Content of Milk Varieties," Cornell University. Retrieved from the Internet May 19, 2015. <URL: http://web.archive.org/web/20070703200307/http://www.milkfacts.info/Nutrition%20Facts/Nutrient%20Content.htm>.

European Search Report dated Aug. 8, 2016, in corresponding European application.

Intellectual Property of India Examination Report dated Apr. 16, 2019 for corresponding Indian Application No. 180/CHENP/2014, filed on Aug. 1, 2014; consisting of 5-pages.

* cited by examiner

FOOD SUPPLEMENT COMPRISING AMINO ACID AND CHROMIUM

FIELD OF THE INVENTION

The invention relates in a first aspect to a food supplement comprising at least the amino acids leucine, isoleucine, valine, threonine and lysine and at least the mineral Chromium. The invention further relates to food compositions comprising the food supplement as well as uses of both.

BACKGROUND OF INVENTION

The metabolic syndrome has become an important health issue world-wide. There is a striking increase in the prevalence of metabolic disorders included in the metabolic syndrome, such as abdominal obesity, type 2 diabetes, atherosclerotic cardiovascular disease (CVD), dyslipidaemia and hyperinsulinaemia.

The diet is one life style factor to be used in the combat against the metabolic syndrome and improved nutrition was recently identified as the single most important tool to reduce the disease burden in the European countries. Several dietary factors and/or properties have been identified as protective adjunct to the metabolic syndrome. A low glycaemic index (GI) diet has thus been associated with a reduced risk of developing diabetes and CVD. Also the type and amount of lipids, and the type and amount of dietary fibre may affect metabolic risk parameters. Certain food groups have further been associated with a lower risk of metabolic syndrome. The progression of the metabolic syndrome proceeds through a step-wise deterioration of metabolic events where deterioration of insulin sensitivity appears to have a key role in a "vicious circle" of hyperinsulinaemia and insulin resistance. Food factors which improve the metabolic control of full-blown manifestations of the metabolic syndrome in subjects with e.g. type 2 diabetes and dyslipidaemia, can therefore be expected to be preventive against this syndrome, whereas food factors inducing high blood glucose and insulin responses may have the opposite effect.

The lower insulin demand with e.g. low-GI foods facilitates blood glucose regulation in situations of impaired insulin sensitivity and in case of impaired insulin secretion, thus providing a therapeutic tool in the management of type 2 diabetes. Pharmaceutical treatment of this conditions, involve different regimens such as insulin secretagouges e.g. sulfonylureas, insulin sensitisers e.g. metformin and thiazolidinediones, or exogenous insulin therapy. From a diet perspective, glucose is the major insulin secretagogue. Recent findings suggest that certain proteins and amino acids also stimulate insulin secretion; directly and/or indirectly by stimulating incretin release. Food derived insulin secretagouges offers advantages compared with traditional pharmaceuticals (e.g. sulfonylureas) in that the insulin secretion only occurs concomitantly with increased blood glucose levels.

Protein induced insulin secretion also circumvents negative side effects that may be associated with certain antidiabetic drugs.

WO200784059 describes a protein composition comprising an amino acid mixture comprising leucine, isoleucine, valine, lysine and threonine in an amount from about 35 to about 90 g/100 g of the total amount of the amino acid part. The composition is useful for control of blood glucose levels in a mammal.

However, there remains a need for new alternative and/or improved compositions which may be useful to regulate blood glucose and thereby reduce or regulate metabolic syndrome, which is increasing worldwide.

SUMMARY OF THE INVENTION

It has been surprisingly found that the ingestion of the food supplement of the invention has a synergistic effect on the reduction in the postprandial glucose level.

The food supplement of the invention comprises at least the amino acids leucine, isoleucine, valine, threonine and lysine as well as Chromium. The combination of these amino acids and Chromium has a synergistic effect reducing the amount of insulin required to reduce blood glucose. This is important for individuals with reduced insulin sensitivity.

The suggested mechanism for the actions of Chromium, particularly in muscle, is described here. Chromium is transported in the blood bound to the carrier protein transferrin, which then binds to its receptor on the cell membrane and is internalized via endocytosis. This process is activated by the insulin-stimulated migration of transferrin receptors to the cell membrane. Once in the cell, chromium is released from transferrin and immediately binds to a LMWCr complex, becoming a part of the insulin signalling amplification system by enhancing tyrosine kinase activity. This process results in an increase in insulin sensitivity.

Without wishing to be bound by theory, it is believed that the amino acid mixture of the food supplement of the invention acts to enhance the insulin release from the insulin-producing cells whereas the Chromium acts to improve insulin sensitivity of these cells.

Surprising synergistic effects are achieved by using these two mechanisms simultaneously, as is shown in Table 5. The data show that the inventive supplement leads to a reduction of blood glucose which is the same or somewhat lower compared to 5AA only. However, the amount of insulin required to achieve the reduction of glucose is only half when the invention supplement is administered. The effect is not merely additive, as the effect is substantially improved as compared to administering the components separately.

Thus the invention relates in a first aspect to a food supplement comprising amino acids and at least one mineral wherein a) the amino acid content consists of leucine, isoleucine, valine, threonine, lysine, and optionally tryptophan and/or taurine; and b) the mineral content comprises at least chromium. The food supplement of the invention may also further comprise one or more of Magnesium, and Calcium.

In a second aspect the invention relates to a food composition comprising a food supplement of the invention.

In a third aspect the invention relates to the use of the food supplement in the manufacture of a food composition. In a fourth aspect the invention relates to the use of the food supplement or the food composition for the treatment, controlling or prevention of diseases or conditions related to metabolic syndrome, diabetes or obesity or in the promotion of satiety, weight loss or maintenance of desired body weight.

In a fourth aspect the invention relates to the use of said food supplement or food composition, dosage product, pharmaceutical or medicament for the treatment, controlling or prevention of diseases or conditions related to metabolic syndrome, diabetes or obesity or in the promotion of satiety, weight loss or maintenance of desired body weight.

Definitions

In the context of the present application and invention, the following definitions apply:

The term "food supplement" refers to a composition which by its addition enhances a food. A food supplement may be added to a food before, during or after preparation of said food. A food supplement may also however be ingested on its own, either before, during or after a meal, or in between meals.

The term "probiotic bacteria" is intended to mean any micro-organism which after administration exercise health beneficial effects, within the mammal it is administrated to.

The term "insulin-associated diseases or conditions" includes diabetes type II, IRS, MetS, IR, insulin sensitivity, IGT, low grade systemic inflammation and hyperinsulinemia as defined below, and related disorders.

The term "Insulin Resistance Syndrome" (IRS) is used interchangeably with the term "Metabolic syndrome" (MetS) and refers to a cluster of dysfunctions and metabolic risk factors which identifies individuals with increased risk of type-2 diabetes and cardiovascular disease. IRS or MetS may be characterized by at least two of the following abnormalities: insulin resistance, hyperinsulinemia, impaired glucose tolerance, hyperlipidemia, hypercholesterolemia, hypertension, and abdominal obesity The term "Insulin resistance" (IR) refers to a condition with impairment of insulin receptor signalling and a condition of impaired ability for glucose regulation.

The term "Insulin sensitivity" refers to a measure of degree of insulin action, with an insulin sensitive condition corresponding to a normal insulin receptor signalling and normal glucose metabolism.

The term "Impaired glucose tolerance (IGT)" refers to a pre-diabetic condition which is characterized by lowered insulin sensitivity in the fasting state, and/or post-prandial blood glucose responses above normal following a glucose challenge.

The term "Hyperinsulinemia" refers to a condition with elevated insulin levels.

The term "GI" refers to Glycaemic Index, that is the post-prandial glycaemic response (incremental glycaemic area under curve) to a carbohydrate test product expressed as a percentage of the corresponding response (incremental glycaemic area under curve) with a carbohydrate equivalent amount of a reference product or pure glucose taken by the same subject. In the literature GI refers to a time period up to 1, 5 or 2 hours post meal. With a white wheat bread as reference product, GI values are approximately 38% higher than with pure glucose as reference. The GI values presented in the present application have been obtained using a white wheat bread as a reference product.

The term "Glycaemic profile", GP, is defined as the duration (min) for the incremental post-prandial glycaemic response divided by the incremental glucose peak (min/mM) elicited by a food. GP may be a better predictor of acute postprandial insulin demand, subjective rating of satiety, and of second meal voluntary food intake compared to GI (see Rosen et al, Nutrition Journal 2009).

The term "dose" is used interchangeably with "serving" and "portion". A dose is intended to mean an amount which provides an effective amount of the food supplement or food composition comprising the food supplement. An effective amount is one that is sufficient to lower the amount of insulin required to lower blood glucose. Such tests are known to the person skilled in the art.

DETAILED DESCRIPTION

The present invention in a first aspect relates to a food supplement comprising amino acids and at least one mineral wherein a) the amino acid content consists of leucine, isoleucine, valine, threonine, lysine, and optionally tryptophan and/or taurine; and b) the mineral content comprises at least chromium.

The invention provides a food supplement which when administered, by itself or in a food composition, leads to a substantially lower insulin demand compared to a food supplement with only amino acids (see e.g. Table 5). This is beneficial for all individuals, and in particular for those who display reduced insulin sensitivity e.g patients with diabetes and subjects with the metabolic syndrome. Such individuals do not respond with adequate insulin release when blood glucose increases, leading to prolonged increased levels of glucose in the blood. High blood glucose levels are correlated with vascular complications in the longer term, leading to eg. cardiovascular disease and associated macro- and microangiopathies, loss of sight etc. In particular, elevated and oscillatory postprandial glycaemic episodes may promote formation of inflammatory cytokines, which are associated with endothelial damage and cardiovascular disease. Such oscillatory episodes are circumvented by the intervention here described Thus, the invention presents a well-characterised, simple and effective way to reduce blood glucose levels after a meal. One advantage of the invention is that a food supplement or food composition of the invention may be administered at the same time as the meal is ingested, delivering the effects only at the time it is needed.

A further advantage of the well-characterised food supplement or food composition of the invention, is that it provides substantial effect while avoiding excess protein and caloric intake for the subject.

The Food Supplement-Amino Acids

The amino acid content of said food supplement consists of at least of leucine, isoleucine, valine, threonine and lysine. In one embodiment the amino acid content of said food supplement consists of leucine, isoleucine, valine, threonine and lysine. In further embodiments of this aspect of the invention, the amino acid content of said food supplement consists of leucine, isoleucine, valine, threonine and lysine and optionally tryptophan and/or taurine. Thus in one embodiment the amino acid content of said food supplement consists of leucine, isoleucine, valine, threonine, lysine and tryptophan. In a further embodiment the amino acid content of said food supplement consists of leucine, isoleucine, valine, threonine, lysine and taurine. In yet a further embodiment, the amino acid content of said food supplement consists of leucine, isoleucine, valine, threonine, lysine, taurine and tryptophan.

The food supplement may have the following distribution of amino acids expressed as % of sum of amino acid content (see Table 1):

TABLE 1

One example of the distribution of amino acids.

| Distribution of amino acids | Percent of total amino acid content in food supplement |
|---|---|
| Leucine | 15-45 |
| Isoleucine | 5-35 |
| Valine | 10-20 |
| Threonine | 17-27 |
| Lysine | 13-23 |
| Taurine (if present) | 15-45 |
| Tryptophan (if present) | 3-35 |

The amino acids may each independently be present in amounts from 1 to 80%, such as from 10-50, 10-40, 10-35, 10-25%, such as from 6-12%, 7-15%, from 5-35%, 40-60%, 50-75%, 46-37%, 3-16%, such that the sum of all present amino acids is 100%.

In one embodiment, leucine is present in from in from 1 to 80%, such as from 10 to 40%, such as from 10-50, 10-40, 10-35, 10-25%, such as from 6-12%, 7-15%, from 5-35%, 40-60%, 50-75%, 46-37%, 3-16%, or such as 25-29%, such as 25%, 26%, 27%, 28%, 29%.

In one embodiment, isoleucine is present in from 1 to 80%, such as from 10 to 40%, such as from 10-50, 10-40, 10-35, 10-25%, such as from 6-12%, 7-15%, from 5-35%, 40-60%, 50-75%, 46-37%, 3-16%, or such as 11-14%, such as 9%, 10%, 11%, 12%, 13%, 14%.

In one embodiment, valine is present in from 1 to 80%, such as from 10 to 40%, such as from 10-50, 10-40, 10-35, 10-25%, such as from 6-12%, 7-15%, from 5-35%, 40-60%, 50-75%, 46-37%, 3-16%, or such as 11-14%, such as 13%.

In one embodiment, threonine is present in from 1 to 80%, such as from 10 to 40%, such as from 10-50, 10-40, 10-35, 10-25%, such as from 6-12%, 7-15%, from 5-35%, 40-60%, 50-75%, 46-37%, 3-16%, or such as 25-29%, such as 25%, 26%, 27%, 28%, 29%.

In one embodiment, lysine is present in from 1 to 80%, such as from 10 to 40%, such as from 10-50, 10-40, 10-35, 10-25%, such as from 6-12%, 7-15%, from 5-35%, 40-60%, 50-75%, 46-37%, 3-16%, or such as 18-29%, such as 18%, 19%, 20%, 21%, 22%, 23%, 24%, 25%, 26%, 27%, 28%, 29%.

In one embodiment, tryptophan is present in from 1 to 80%, such as from 10 to 40%, such as from 10-50, 10-40, 10-35, 10-25%, such as from 6-12%, 7-15%, from 5-35%, 40-60%, 50-75%, 46-37%, 3-16%, or such as 25-29%, such as 25%, 26%, 27%, 28%, 29%, or for example 36, 39, 48, 66, 67, 73%.

In one embodiment taurine is present in from 1 to 80%, such as from 10 to 40%, such as from 10-50, 10-40, 10-35, 10-25%, such as from 6-12%, 7-15%, from 5-35%, 40-60%, 50-75%, 46-37%, 3-16%, or such as 25-29%, such as 25%, 26%, 27%, 28%, 29%, or for example 36, 39, 48, 66, 67, 73%.

The rate at which the amino acids are released during digestion and absorbed into the circulation is affected by the form in which the amino acids are present Amino acids present in a form which is soluble, rapidly digested and/or easily absorbed enhances the plasma concentration of amino acids and promotes insulin secretion. Thus the amino acid content of the food supplement according to the invention may be present in a form selected from the group of: peptides consisting of one or more of the amino acids, free amino acids, or a mixture thereof. The peptides may consist of 2, 3, 4, 5 or 6 amino acids, or more, for example up to 10 amino acids or up to 20 amino acids, selected from the group of leucine, isoleucine, valine, threonine, lysine and optionally tryptophan and/or taurine according to the above. The peptides need not be identical to each other. Instead the mixture containing peptides may differ in for example amino acid sequence and/or length. Also from taste point of view it may be suitable for certain amino acids to be present as part of a peptide.

One or more of the amino acids or peptides may be synthesized or may be derived from for example one or more of the sources selected from the group comprising whey, soy-, casein-, oat-, egg-, blood-, pea-, barley-, fish protein, gelatine and α-lactalbumin.

If one or more of the amino acids are derived from whey, the whey may be obtained from any mammal source such as from cows, goats. If one or more of the amino acids are obtained from a plant material such as soy, they may be obtained from for example genetically modified cultivars, such as by having an increased content of one or more of the amino acids.

The Food Supplement-Chromium

The food supplement of the invention further comprises at least Chromium. The combination of Chromium with the amino acids in the food supplement according to the invention has synergistic beneficial effects on the acute glucose regulation.

Chromium may be present such that the amount present in each dose is for example least 10, for example at least 15, such as at least 20, at least 25, at least 30, at least 40, at least 50, at least 60, such as at least 70, at least 100, at least 200, at least 150, at least 250, at least 300, at least 400, at least 500, such as from 10 to 70, 25 to 50, 50 to 65, 60 to 65, from 50 to 70, 20 to 30 or 1 to 12 micrograms per dose. In certain embodiments Chromium is present in amount of 50, 55, 60, 63, 64, 65, 67, 68, 70, 72, 75, 78, 80 micrograms per dose.

The chromium may be present in any form which is suitable for consumption such as for example one or more of chromium picolinate, chromium nicotinate, chromium polynicotinate, chromium propionate, chromium acetylacetonate, chromium-citrate, chromium nicotinate, chromium-dinicocysteinate, Niacin-bound chromium, Amino acid chelates with chromium, chromium chelavite, or combinations thereof.

In one embodiment, chromium is present as Chromium picolinate, such as chromium tripicolinate, chromium dipicolinate, chromium monopicolinate or combinations thereof. In a further embodiment, chromium is present as Chromium tripicolinate.

In another embodiment, chromium is present as Chromium dinicocysteinate (CDNC). CDNC and chromium picolinate have both shown positive effects on different metabolic markers for longer term glucose regulation.

The percentage of Chromium in chromium tripicolinate (i.e. chromium (III) picolinate) is 12.43%, meaning that 1000 micrograms Chromium (III) Picolinate contains 125 micrograms Chromium. Sometimes this is expressed as 100 micrograms Chromium (III) picolinate equals 19.2 micromoles Chromium, i.e. 12.4 micrograms Chromium.

The food supplement may further comprise one or more further minerals, which have beneficial semi-acute (i.e ranging over several meals) or long term (over several days) effects on glucose metabolism. Examples of beneficial effects are lowering of insulin response and increased insulin sensitivity as compared to these in the subject before taking the supplement. Examples of such minerals which have such long term effects are for example Calcium and/or Magnesium.

Thus, in one embodiment the food supplement of the invention further comprises one or both minerals selected from Magnesium and Calcium.

Magnesium may be present in amounts of for example 600 mg/serving, such as 100-600 mg per serving. Calcium may be present in amounts such as for example 200, 300, 400, 400-1200, 500-1300 mg per serving or per dosage food supplement. Magnesium may be present in amounts of for example from 10 to 100 mg/per dose or serving, such as for example 10 to 70 mg, 10 to 50 mg, 10 to 40 mg, 10 to 23 mg, or for example from 15 to 60 mg, or 15 to 35 mg/dose or serving. For example, Magnesium may be present in amounts of for example, 15, 20, 23, 40, 50, 65, 70, 80, 85, or 90 mg/dose or serving.

Calcium may be present in amounts of for example from 25 to 250 mg/per dose or serving, such as for example 25 to 220, 30 to 200, 30 to 170, 30 to 150, 30 to 120, 30 to 100, 30 to 70, 30 to 50 mg/per dose or serving, or for example 25 to 75, 25 to 65, 25 to 45 mg/dose or serving.

The food supplement may further comprise one or more further components which facilitate the uptake/absorption of one or more of the minerals comprised in the supplement of the invention. Examples of such components are acids such as ascorbic acid (Vitamin C). Vitamin C may be present in amounts of for example 0.5 g, 1 g, 1.5 g, 2 g, 2.5 g or 3 g/day such as 0.5-0.75 g per serving or per dosage food supplement.

In further embodiments the food supplement may contain antioxidants, which have an important function in protection in inflammation and MetS. One example of an antioxidant is Vitamin C.

In further embodiments the food supplement of the invention may comprise one or more probiotic microorganisms. Probiotic microorganisms are known to beneficially affect the barrier of the colonic epithelium, and to reduce the risk of influx of pro-inflammatory factors into the circulation. In addition to this, probiotics may beneficially affect carbohydrate and lipid metabolism.

The food supplement of the invention may thus comprise at least one probiotic microorganism strain. Examples of suitable probiotic micro-organisms include yeasts such as *Saccharomyces, Debaromyces, Candida, Pichia* and *Torulopsis*, moulds such as *Aspergillus, Rhizopus, Mucor,* and *Penicillium* and *Torulopsis* and bacteria such as the genera *Bifidobacterium, Bacteroides, Clostridium, Fusobacterium, Melissococcus, Propionibacterium, Streptococcus, Enterococcus, Lactococcus, Staphylococcus, Peptostreptococcus, Bacillus, Pediococcus, Micrococcus, Leuconostoc, Weissella, Aerococcus, Oenococcus* and *Lactobacillus*. Specific examples of probiotic microorganisms are: *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei* subsp. *casei, Lactobacillus casei Shirota, Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus reuteri, Lactobacillus rhamnosus (Lactobacillus GG), Lactobacillus sake, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Staphylococcus carnosus, Staphylococcus xylosus, Lactobacillus acidophilus, Lactobacillus thermofilus, Lactobacillus bulgaricus, Lactobacillus plantarum, Lactobacillus reuteri, Bifidobacterium bifidum, Bifidobacterium longum. Caseii, Lactobacillus iners.*

For example, the probiotic microorganism may be selected from the group consisting of *Lactobacillus acidophilus, Lactobacillus thermophilus, Lactobacillus bulgaricus, Lactobacillus plantarum, Lactobacillus reuteri, Bifidobacterium bifidum, Bifidobacterium longum. Caseii* and *Lactobacillus iners.*

The probiotic microorganisms may be in powdered, dried form; especially in spore form for microorganisms which form spores. Further, if desired, the probiotic microorganism may be encapsulated to further increase the probability of survival; for example in a sugar matrix, fat matrix or polysaccharide matrix.

The relationship between Chromium and the sum content of the amino acids leucine, isoleucine, valine, threonine and lysine in a dose may be for example between 4 and 10 microgram Chromium per g sum content of said amino acids. Further examples include 4-9 micrograms, 5-10 micrograms, 6-10 micrograms, 5-10 micrograms, and 5-9 micrograms Chromium per g sum content of said amino acids. Further examples are 1, 2, 3, 4, 5, 6, 7, 8, 9, 10, 11, 12, 13, 14 or 15 microgram Chromium per g sum content of said amino acids.

A dose of the food supplement or the food composition comprises an amount of the amino acids leucine, isoleucine, valine, threonine and lysine and Chromium sufficient to reduce the amount of insulin required for lowering the blood glucose.

A dose may for example comprise the amino acids leucine, isoleucine, valine, threonine and lysine in a sum content of for example 1-100 g, for example 2-80 g, 2-75 g, 3-65 g, 5-50 g, or for example 1-20 g, 2-18 g, 2-16 g such as 5-10 g, or for example 4, 5, 6, 7, 8, 9, 10, 11, 12 grams; or for example 10, 15, 18, 20 grams.

Food Compositions

In a second aspect the invention relates to a food composition comprising the food supplement of the invention.

Examples of embodiments of this aspect of the invention are food compositions, feeds, drinks, functional foods, functional feed, nutraceuticals, nutritional supplements, medicaments and pharmaceuticals comprising the food supplement of the invention.

In one embodiment of this aspect of the invention, the food composition consists of the food supplement of the invention dispersed or dissolved in a liquid or semi-liquid such as for example water, juice, yoghurt, milk, soymilk, oatmilk or other drink or drinkable food composition, or other food composition.

In an embodiment of this aspect of the invention, the food supplement may be present in the food composition for example in 0.5%, 0.75%, 1%, 1.5%, 1-5%, 2%, 5%, 5-8%, 1-10%, 10%, 20%, 30%, 40%, 40-60%, 60%, 70% such as 80%, for example 85%, 90%, 95% of the food composition by weight.

The food supplement may be present in an amount of for example 1, 2, 4, 5, 7, 8, 10, 13, 15, 16, 18, 19, 20, 22, 24, 25, 28, 30, 31, 35, 40, 45, 50, 55, 60, 65, 70, 75, 80, 85 or 90 g/100 g of the total food composition.

In another embodiment the food composition of the invention comprises a protein base, such as a protein hydrolysate, to which the food supplement of the invention is added.

The food composition may include other components such as carbohydrates, dietary fibre, lipids, essential vitamins, minerals, flavouring agents, texturizers, stabilizers, spices such as e.g. cinnamon, fruit and berries and extracts thereof. The food composition may also contain vinegar and olive oil. The vinegar has additional benefits in relation to blood glucose regulation in that the presence of acetic acid will reduce the rate of gastric emptying hence slowing down the rate of glucose delivery to the blood. Examples of commonly used flavouring agents may be found in Burdock 2004; Fenarolis Handbook of Flavor Ingredients; Fifth Edition, Taylor and Francis CRC Press; Yannai 2003; Dictionary of Food Compounds with CD-ROM, additives, flavours and ingredients, Taylor and Francis CRC Press, e.g. citrus, strawberry, vanilla.

In addition, the food supplement and/or food product may be a powder to be reconstituted in water by the consumer before use as preferred.

Applications in athletes may include enclosure of the invented product in mixture with a readily digestible carbohydrate source such as a mixture of glucose, maltose and malto-dextrins in proportions to prevent nausea, micronutrients, minerals and vitamins. The food composition may be ingested as a post-event meal that is, immediately after the strenuous exercise.

The food composition of the invention may appear as a solid, a semi-solid such as a cream or paste, a gel, a liquid, a dispersion, a suspension or an emulsion, a powder for dissolution, or in any desired form. The composition may appear, for example, in the form of any kind of food, feed, drink, functional food and functional feed, e.g. as a cereal product such as flakes, bars, breads, cookies and biscuits, as juice, jam, spread, soft drink, oat suspension, soya milk, meat product, dairy products such as yoghurt, chocolate, cheese, pudding and other dairy desserts, spreadable products, frozen desserts and ice-cream, malt drink, coffee, tea, sport drink, meal replacement, gruel, porridge, ready to eat meals, infant formula, baby food; in the form of a pharmaceutical composition and medicament, e.g. as a powder, an aggregate, a granulate, a tablet, a coated tablet, a lozenge, a capsule, a drink, a syrup, a composition for tube feeding, for enteral intake, for oral administration and for enteral administration.

In one embodiment the food supplement or composition of the invention is formulated as a tablet. The ingredients of the food supplement of this invention may be contained in acceptable excipients and/or carriers for oral consumption. The actual form of the carrier may not be critical. The carrier may be a liquid, gel, gelcap, capsule, powder, solid tablet (coated or non-coated), tea or the like. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, agar, lactose, methylcellulose, povidone, carboxymethylcellulose, corn starch, and the like (including mixtures thereof). The various ingredients and the excipient and/or carrier are mixed and formed into the desired form using conventional techniques. Dose levels/unit can be adjusted to provide the recommended levels of ingredients per day in a reasonable number of units. The dietary supplement may also contain optional ingredients including, for example, herbs, vitamins, minerals, enhancers, colorants, sweeteners, flavorants, inert ingredients, and the like. Such optional ingredients may be either naturally occurring or concentrated forms. Selection of one or several of these ingredients is a matter of formulation, design, consumer preference and end-user. The amounts of these ingredients added to the dietary supplements of this invention are readily known to the skilled artisan.

In another embodiment the food supplement or food composition may be packaged in individual dosage form; for example a sachet, such as a sachet containing a powder or granulate, which enables the consumer to select to what foods the food supplement of the invention shall be added. In one embodiment, the food supplement or food composition of the invention may be in a dry form for example in powder or granulate form, to be reconstituted in water or liquid by the consumer before use as preferred.

Uses

In a third aspect the invention relates to the use of the food supplement of the invention in the manufacture of a food composition such as a feed, a drink, a dosage form, a functional food, a functional feed, a pharmaceutical or a medicament.

The food compositions according to the invention can be prepared by conventional techniques, including, for example, mixing the food supplement of the invention with at least one edible or pharmaceutically acceptable component, or, alternatively, by mixing the food supplement, together with one or more of said edible or pharmaceutically acceptable components, optionally followed by bringing the obtained food composition in a desired form by conventional techniques.

The food composition of the invention may be manufactured by addition of the food supplement of the invention at one or more suitable stages in production.

In a fourth aspect the invention relates to the use of said food supplement or food composition, dosage product, pharmaceutical or medicament for the treatment, controlling or prevention of diseases or conditions related to metabolic syndrome, diabetes or obesity or in the promotion of satiety, weight loss or maintenance of desired body weight.

Examples of this use are the use to reduce release of insulin, improve insulin sensitivity (increased) and/or insulin resistance (reduced).

The food supplement or food composition of the invention may also be used for persons such as those, with reduced insulin secretory capacity and/or insulin resistance such as type 2 diabetic patients, persons with impaired glucose tolerance, subjects in a catabolic state (post-operative, elderly, anorexia nervosa) and may be used in enteral nutrition. In addition, the food supplement and/or food composition of the invention is suitable for use in athletes recovering from strenuous exercise.

This aspect of the invention further relates to the use of the food supplement of the food composition of the invention in promoting of satiety, reducing hunger, controlling appetite, and in weight loss or maintenance of desired body weight.

The food supplement or food composition of the invention may be ingested prior to or during the initial phase of the meal in subjects, such as subjects with type 2 diabetes or glucose intolerance. Due to the rapid stimulation of insulin release, it is possible to adjust the timing to match the requested effect. In one embodiment the food supplement or food composition is ingested before a meal. For example between 1 hour and 5 mins before a meal such as 45 min, 30 mins, such as 20 mins, 15 min, 10 mins before a meal. In other embodiments the food supplement or food composition is ingested together with the meal. The food supplement or food composition may also be ingested after a meal, or as needed after a meal. Examples include immediately after, or 5, 10, 15, 20, 30 mins after the meal.

In other embodiments the food supplement or food composition may be ingested for example once a day, or several times a day, such as with each meal.

In a further aspect the invention relates to the use of the food supplement of the invention or the food composition of the invention in combination with pharmaceuticals directed for treatment, controlling or prevention of diseases or conditions related to metabolic syndrome, diabetes or obesity or in the promotion of satiety, weight loss or maintenance of desired body weight.

In a further embodiment, the present invention relates to the use of a food supplement or food composition according to the present invention for modifying the glycaemic response to the meal in humans or mammals that are healthy, at risk for, or suffering from one or more diseases related to insulin regulation.

In a further aspect of the present invention relates to the use of the food supplement or food composition according to the invention, for treating, controlling or preventing diseases or conditions associated with metabolic or insulin resistance syndrome.

Examples of disease or conditions associated with insulin regulation include metabolic syndrome, insulin resistance, diabetes, obesity, or symptoms and conditions associated with these disorders. The use may be for example by oral and/or enteral intake or administration, for example of a dose in conjunction with meals.

In a further embodiment the present invention relates to a method of treatment, comprising administering to a subject in need of such treatment an effective amount of a food supplement or food composition of the invention in a suitable dosage form. In one embodiment, the doses are taken together with, or shortly before, e.g. 15 minutes before, the main meals, e.g. in the morning, at noon, and in the evening.

Yet a further embodiment of the present invention is the use of the food supplement or food composition of the invention in the promotion of satiety, control of appetite or weight loss or in the maintenance of body weight.

The invention further provides a method of improving the bodily appearance of a mammal which comprises orally administering to said mammal a food supplement or food composition of the invention, in a dosage effective to influence the glucose metabolism, and repeating said dose until a cosmetically beneficial loss of body weight has occurred.

The following examples are intended to illustrate, but not to limit, the invention in any manner, shape, or form, either explicitly or implicitly.

EXAMPLES

Example 1

Test Products

Four different beverages were tested by the inventors; one reference, one with only the amino acid mixture, one with only CrPic, and one combining the amino acid mixture with CrPic. The amino acids used were L-leucine, L-isoleucine, L-lysine, L-valine and L-threonine.

The reference ("Ref") drink was made out of tap water and aroma, poured into 330 mL bottles and carbonated with a Table Top Carbonator CF-121 (Omve) set at 10 g $CO_2$/L.

The beverage with CrPic ("CrPic") was prepared by dissolving one thawed pellet of concentrated CrPic solution (4.0 grams) in 308.0 grams of carbonated tap water and thereafter 0.19 grams of aroma was added. Additional $CO_2$ was added just before serving with a Soda Streamer to mimic the amount in the Ref drink.

The beverage with amino acids ("5AA") was prepared by dissolving 6.9 grams of the amino acid mixture in 305.1 grams of carbonated tap water and thereafter 0.19 grams of aroma was added. Additional $CO_2$ was added just before serving with a Soda Streamer to mimic the amount in the Ref drink. See Table 7 for composition of amino acid mixture.

The beverage with amino acids and CrPic ("5AA+CrPic") was prepared by dissolving 6.9 grams of the amino acid mixture and one thawed pellet of concentrated CrPic solution (4 grams) in 301.1 grams of carbonated tap water and thereafter 0.19 grams of aroma was added. Additional $CO_2$ was added just before serving with a Soda Streamer to mimic the amount in the Ref drink.

The test meals consisted of sandwiches made of white wheat bread (Dollarfranska, Lockarps, Lockarp, Sweden), contributing with 50 grams of available starch, and the test drinks. The white wheat bread was spread with 10 grams of butter (Bregott, Arla, Stockholm, Sweden) and 24 grams of orange marmalade (kindly provided by Önos, Procordia Food, Eslöv). The sandwiches provided 9 grams of protein and an additional amount of carbohydrates from the marmalade and butter of 14 grams. A schematic overview of the composition of the different test meals is found in Table 2.

TABLE 2

Distribution of macronutrients in the four different test meals[2]

| | Ref meal | CrPic meal | 5AA meal | 5AA + CrPic meal |
|---|---|---|---|---|
| Carbohydrates[1] | 70.8 g | 70.8 g | 70.8 g | 70.8 g |
| Protein | 9.1 g | 9.1 g | 16.1 g | 16.1 g |
| Fat | 11.7 g | 11.7 g | 11.7 g | 11.7 g |

[1]Of which 50 g available starch from bread

[2]CrPic = Chromium tripicolinate; 5AA = 5 amino acid mixture; see Table 7 for composition.

Study Design

Nineteen healthy subjects, 11 men and 8 women, aged 38-60 (51±1 years; mean±SEM) and with body mass indexes of 24-30 (27.3±0.3 kg/m2; mean±SEM) were included in the study. All subjects had normal fasting blood glucose levels (5.6±0.1 mmol/L, mean±SEM).

The test subjects were instructed to eat a dinner of own choice (but with a low content of fiber) as well as an evening meal consisting of white wheat bread and a beverage, and to eat the same meals the evening before every test occasion. After the white wheat bread meal at around 9-10 p.m., the subjects were thereafter to restrain from ingesting anything but maximum a half glass of water on the morning of the test occasion.

Upon arrival at the laboratory at 07.45 on the test day, the subjects were sat to rest before a fasting capillary blood sample was drawn. Immediately thereafter, the test meal was served and a digital timer was started. Together with the drinks, a ham sandwich meal was served, containing 64 g available carbohydrates, 9.1 g protein and 11.7 g fat. The subjects were instructed to finish the meal in 10-15 minutes and to alternate between eating and drinking. All meals were well tolerated, and the subjects had no problems finishing eating within the 10-15 min period.

All test subjects gave their informed consent and were aware of the possibility of withdrawing from the study at any time they desired. The Ethics Committee of the Faculty of Medicine at Lund University approved the study.

Blood Sampling and Analysis

Capillary blood samples were taken at fasting and 15, 30, 45, 60, 90, 120 and 180 min after the ingestion of the meal for the analysis of blood glucose and serum insulin.

Blood glucose was immediately analyzed in serum with the use of a B-glucose analyzer (Hemocue AB, Ängelholm, Sweden). Serum tubes were centrifuged for 5 min (3000 rpm) and serum was frozen at −18° C. for the measurement of insulin. The serum insulin measurement was performed on an integrated immunoassay analyzer (CODA open Microplate System, Bio-Rad Laboratories, Hercules, Calif.) by using an enzyme immunoassay kit (Mercodia Insulin ELISA, Mercodia AB, Uppsala, Sweden). The kit is a solid-phase two-site enzyme immunoassay, which uses two monoclonal antibodies that are directed against two separate antigenic determinants located on the insulin molecule (direct sandwich technique).

An appetite profile was determined by the use of 100 mm Visual Analogue Scales (VAS) for "hunger", "satiety" and "desire to eat", respectively. The scales were anchored with "not at all" and "extremely". The subjects were instructed to rate the point at the scale which best conformed to their feeling at the time in question. The ratings were made at the same time points as for the blood sampling, i.e. 8 times per test session.

Calculations and Statistical Methods

In total 19 subjects participated in the study. For glucose and insulin data there are 18 subjects for the "5AA" meal due to illness of one test person. For subjective appetite ratings there are 18 subjects for the "5AA+CrPic" meal since one test person missed filling in the VAS during the test.

All the data is expressed as means±SEM and calculated in Minitab (Minitab Inc., State Collage, Pa.). The iAUC (incremental area under the curve) for glucose and insulin, respectively, was calculated according to the trapezoidal method, excluding areas below the fasting level. Total areas under the curve were calculated for satiety, hunger and desire to eat, respectively, using GraphPad (GraphPad Prism, version 5, GraphPad Software, San Diego, Calif., USA). Incremental peaks (iPeaks) were calculated for glucose and insulin curves, respectively, as their maximum elevation of the values from the baseline. GI and II, respectively, were calculated by dividing the iAUC (0-120 min) of the test meal with the corresponding reference meal taken by the same subject. The glucose profile (GP) was calculated by dividing the duration time (the time the curve stayed above baseline) by the iPeak.

To evaluate statistical significances for iAUCs of glucose and insulin, as well iPeaks, GI, II and GP, analysis of variance (ANOVA) was used followed by Tukey's pair-wise comparison. Incremental values were used for the calculations. For satiety, hunger and desire to eat, analysis of variance with covariat (ANCOVA) was used. For calculation of ANCOVA the total area values were used and the values at 0 as covariates (Minitab Inc., version 14 and 16, State College, Pa.).

Results

Postprandial Blood Glucose Response

The fasting blood glucose values did not differ significantly between the test occasions. Thus, the delta values for the blood glucose response were used in further calculations.

In Table 3, the iAUCs for the blood glucose response for the time interval 0-60 min, 0-120 min and 0-180 min is shown. Displayed in the table is also the change in the mean values of the iAUCs expressed as a percentage of the mean iAUC for the reference meal. Significant lowering of glucose iAUC was observed at the time intervals 0-60 and 0-120, respectively. During 0-60: for 5AA+CrPic compared to Ref and compared to CrPic; for 5AA compared to Ref. During 0-120: for 5AA+CrPic compared to the reference.

TABLE 3

Blood glucose iAUC[1] (incremental area under the curve) for the time intervals 0-60 min, 0-120 min and 0-180 min in mmol · min/L.

|  | iAUC 0-60 min mmol min/L | Change[2] % | iAUC 0-120 min mmol min/L | Change[2] % | iAUC 0-180 min mmol min/L | Change[2] % |
| --- | --- | --- | --- | --- | --- | --- |
| Ref. | 114.8 ± 8.2$^a$ | — | 200.4 ± 18.1$^a$ | — | 232.2 ± 23.1 | — |
| CrPic | 100.2 ± 9.3$^{ac}$ | −13 | 189.1 ± 20.7$^{ab}$ | −6 | 222.3 ± 25.6 | −4 |
| 5AA + CrPic | 78.5 ± 7.9$^b$ | −32 | 157.7 ± 17.4$^b$ | −21 | 188.3 ± 21.9 | −19 |
| 5AA | 85.2 ± 7.6$^{bc}$ | −26 | 166.3 ± 16.7$^{ab}$ | −17 | 203.9 ± 22.3 | −12 |

[1]Values expressed as mean ± SEM; n = 19 (except for 5AA, n = 18). Products in the same column not sharing the same letter are significantly different, p < 0.05 (ANOVA followed by Tukey's test).

[2]Change (%) in postprandial response as a percentage of the reference meal.

Postprandial Insulin Response

In Table 4, the iAUCs for the insulin response for the time interval 0-60 min, 0-120 min and 0-180 min is shown. Displayed in the table is also the change in the mean values of the iAUCs expressed as a percentage of the iAUC for the reference meal. Significant differences in insulin iAUC were observed for all time intervals. At 0-60: for 5AA compared to the Ref and CrPic. At 0-120: for 5AA+CrPic compared to Ref and CrPic; for 5AA compared to Ref and CrPic. During 0-180: for 5AA+CrPic compared to CrPic; for 5AA compared to Ref and CrPic.

It can be concluded that the same postprandial glucose levels are obtained after both drinks containing 5AA. However, the amount of insulin needed to reach that glucose level is substantially lower in the case of a combination of 5AA with CrPic (comparison presented in Table 5).

TABLE 4

Insulin iAUC[1] for the time intervals 0-60 min, 0-120 min and 0-180 min in nmol · min/L.

|  | iAUC 0-60 min nmol · min/L | Change % | iAUC 0-120 min nmol · min/L | Change % | iAUC 0-180 min nmol · min/L | Change % |
|---|---|---|---|---|---|---|
| Ref. | 8.5 ± 1.2$^a$ | — | 17.0 ± 3.1$^a$ | — | 20.8 ± 4.4$^{ab}$ | — |
| 5AA + CrPic | 10.0 ± 1.2$^{ab}$ | 17 | 20.9 ± 2.9$^b$ | 22 | 24.9 ± 4.0$^{ac}$ | 20 |
| 5AA | 12.1 ± 0.9$^b$ | 42 | 24.2 ± 4.2$^b$ | 42 | 28.9 ± 5.8$^c$ | 39 |

[1]Values expressed as mean ± SEM; n = 19 (except for 5AA, n = 18). Products in the same column not sharing the same letter are significantly different, p < 0.05 (ANOVA followed by Tukey's test).
[2]Change (%) in postprandial response as a percentage of the reference meal

TABLE 5

Comparison between glucose and insulin responses[1] at 0-120 min.

| Meal | Glucose iAUC 0-120 min | Change[2] (%) | Insulin iAUC 0-120 min | Change (%) |
|---|---|---|---|---|
| Ref. | 200.4 ± 18.1$^a$ | — | 17.0 ± 3.1$^a$ | — |
| CrPic | 189.1 ± 20.7$^{ab}$ | −6 | 15.4 ± 1.9$^a$ | −10 |
| 5AA + CrPic | 157.7 ± 17.4$^b$ | −21 | 20.9 ± 2.9$^b$ | 22 |
| 5AA | 166.3 ± 16.7$^{ab}$ | −17 | 24.2 ± 4.2$^b$ | 42 |

[1]Values expressed as mean ± SEM; n = 19 (except for 5AA, n = 18). Products in the same column not sharing the same letter are significantly different, p < 0.05 (ANOVA followed by Tukey's test).
[2]Change (%) in postprandial response as a percentage of the reference meal From Table 5 it can be concluded that the glucose response after 5AA+CrPic is the same or somewhat reduced compared to 5AA only, but only half the amount of insulin is needed to obtain this glucose lowering effect with 5AA+CrPic. Therefore a substantially better effect is obtained with the combination of compounds, rather than serving them separately.

TABLE 6

Composition of the drinks (330 ml carbonated water)

|  | Ref | CrPic | 5AA | 5AA + CrPic |
|---|---|---|---|---|
| 5AA-mix (g) |  |  | 6.94 | 6.94 |
| CrPic solution (μg) |  | 495 |  | 495 |

TABLE 7

Composition of the 5AA-mix

| Amino acid | gram/L | weight ratio | % of total AA | gram/ dose |
|---|---|---|---|---|
| Leu | 5.8163 | 2.1 | 28% | 1.92 |
| Ileu | 2.8030 | 1.0 | 13% | 0.92 |

TABLE 7-continued

Composition of the 5AA-mix

| Amino acid | gram/L | weight ratio | % of total AA | gram/ dose |
|---|---|---|---|---|
| Val | 2.8030 | 1.0 | 13% | 0.92 |
| Thr | 5.6761 | 2.0 | 27% | 1.87 |
| Lys | 3.9242 | 1.4 | 19% | 1.29 |
| Total |  |  |  | 6.94 |

TABLE 8

Amounts of Chromiumpicolinate

|  | g/L | mcg Cr/L | mcg CrPic/dos | mcg Cr/dose |
|---|---|---|---|---|
| CrPic | 0.00150 | 186.45 | 495 | 61.53 |

Example 2: Probiotic Yoghurt 2.5 dl yoghurt containing a probiotic culture was mixed with the food supplement containing amino acid mixture and CrPic as described below in Table 9. The total amount of added amino acids was 9 g and CrPic 400 μg.

TABLE 9

Composition of food supplement

| Amino acids (aa) | % of total aa | g/port |
|---|---|---|
| Leu | 35 | 3.15 |
| Ile | 15 | 1.35 |
| Val | 10 | 0.9 |
| Thr | 23 | 2.07 |
| Lys | 17 | 1.53 |
| CrPic |  | 400 μg |

Example 3

The experiment was performed using a study design identical to the one in Example 1. Only test meals and test subjects differed and are thus described below.

3.1 Test Meals

The test meals always contained a white wheat bread (WWB) (Dollarfranska, Lockarps, Lockarp, Sweden), contributing with 50 g available starch. The bread was spread with 10 g of butter (Bregott, Arla, Stockholm, Sweden) and 24 g of orange marmalade (Önos Apelsinmarmelad, Procordia, Eslöv, Sweden). The test drink, an orange juice, was served together with the bread. One meal contained the juice with amino acids and CrPic (5AA+CrPic meal) and the other contained a reference juice (Ref meal). 150 mL of juice was served with each meal and each meal also contained 100 mL of water. The macronutrient composition of the different meals can be seen in Table 10.

TABLE 10

Total macronutrient composition of the different test meals in the meal study. (Swedish National Food Agency, 2012a, 2012b)

|  |  | 5AA + CrPic meal | Ref meal |
|---|---|---|---|
| Carbohydrates[1] | g | 78.0 | 78.0 |
| Fat | g | 10.5 | 10.5 |
| Protein | g | 16.1 | 9.2 |
| Energy | kcal | 476 | 448 |

[1]Including 50 g carbohydrates from the bread 3.2 Test Subjects 13 health and non-smoking subjects, 7 women and 6 men, volunteered to participate in the study. Their age range was 40-60 years (54±5 years; mean±s) and their body mass index was in the range 24-30 kg/m2 (27.8±2.2 kg/m2; mean±s). All subjects had normal fasting blood glucose levels (5.4±0.4 mmol/L; mean±s). All of the subjects volunteered to participate in the study and gave their informed consent. The subjects were aware that they could withdraw from the study at any time, should they wish to do so. The study was approved by the Ethics Committee of the Faculty of Medicine at Lund University.

3.3 Results

Postprandial Glucose Response

Figure 1:
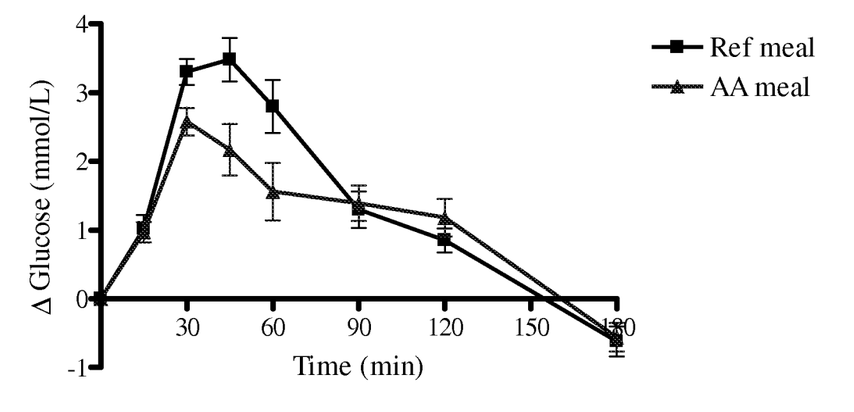
FIG. 1 shows the glycemic response following intake of the 5AA+CrPic meal and the Reference meal, respectively. Values are expressed as mean±SEM; n=13. ■=Ref meal; ▲=AA (5AA+CrPic meal)

The fasting blood glucose values did not differ significantly between the test occasions. Thus, the delta values for the blood glucose response were used in further calculations. In FIG. 1 the mean blood glucose responses for the test subjects are depicted over the whole postprandial period. In Table 11, the iAUCs for the blood glucose response for the time intervals 30-90 min, 0-120 min and 0-180 min, are shown. Displayed in the table is also the change in the mean values of the iAUCs expressed as a percentage of the mean iAUC for the reference meal. In table 12 the iPeak and the GP values are displayed.

From these results it can be concluded that the juice containing 5AA+CrPic is highly effective in lowering the blood glucose response to a white wheat bread based meal. The overall glycaemic response is lowered by 20%, the incremental glucose peak by 25% and the GP is increased by 50%. Taken together this shows that the 5AA+CrPic addition is effective not only in water as described in Example 1 but also in the context of a food vector, in this case an orange juice, which in itself adds more sugars to the meal.

TABLE 11

Glucose iAUC for Ref meal and AA meal, during the time intervals 0-30, 30-90, 0-120 and 0-180 minutes and change in percentage compared to reference

| | 30-90 | | 0-120 | | 0-180 | |
|---|---|---|---|---|---|---|
| Meal | iAUC (mmol · min/L) | Change (%) | iAUC (mmol · min/L) | Change (%) | iAUC (mmol · min/L) | Change (%) |
| Ref meal | 159.6 ± 16.0 | — | 231.9 ± 19.0 | — | 252.8 ± 18.5 | — |
| AA meal | 108.8 ± 18.7* | −31.8 | 181.6 ± 26.9* | −21.7 | 209.0 ± 31.2 | −17.3 |

[1]Values expressed as mean ± SEM; n = 13. The areas of AA meals that are significantly different from the areas of the corresponding Ref meal are market with an asterisk, p < 0.01 (30-90) or p < 0.05 (0-120) with ANOVA.
[2]Change (%) in postprandial response as a percentage of the reference meal

TABLE 12

Glucose iPeak and GP with percentage changes compared to reference for Ref meal and AA meal.

| | ΔiPeak (mmol/L) | | GP (min · L/mmol) | |
|---|---|---|---|---|
| Meal | mean ± SEM | Change (%) | mean ± SEM | Change (%) |
| Ref meal | 3.8 ± 0.3 | — | 39.3 ± 3.8 | — |
| AA meal | 2.9 ± 0.3* | −24.7 | 58.8 ± 6.4* | +49.4 |

The values of AA meals that are significantly different from the values of the corresponding Ref meal are market with an asterisk, p < 0.01 with ANOVA; n = 13.

The invention claimed is:

1. A food supplement dissolved in carbonated water, comprising:
    amino acids;
    at least one mineral, where the amino acid content of the food supplement consists of leucine, isoleucine, valine, threonine and lysine, the sum content of the amino acids being 6.9 grams per dose of the food supplement, leucine is present in an amount of 28%, isoleucine is present in an amount of 13%, valine is present in an amount of 13%, threonine is present in an amount of 27%, lysine is present in an amount of 19%, and the percent calculated based upon the total amino acid content, by weight, in the food supplement; and
    the mineral content comprises 500 μg of chromium picolinate per dose of the food supplement.

2. The food supplement of claim 1, further comprising at least one of the group consisting of magnesium and calcium.

3. The food supplement of claim 1, further comprising at least one probiotic bacteria.

4. The food supplement of claim 1, wherein the amino acids are present in a form selected from the group of peptides consisting of one or more of the amino acids, free amino acids, or a mixture thereof.

5. The food supplement of claim 1, further comprising vitamin C.

6. The food supplement of claim 1, wherein a dose of the food supplement comprises 6 to 12 micrograms of chromium per gram of the amino acids.

7. A method of reducing the postprandial glucose level in a subject where postprandial is the period of 0-180 minutes after the subject consumes a meal, the method comprising:
    administering a dose of a food supplement to the subject between 45 minutes before and 30 minutes after the subject consumes a meal, the food supplement being dissolved in carbonated water, the food supplement comprising:

amino acids; and at least one mineral, where the amino acid content of the food supplement consists of leucine, isoleucine, valine, threonine and lysine, the sum content of the amino acids being 6.9 grams per dose of the food supplement, leucine is present in an amount of 28%, isoleucine is present in an amount of 13%, valine is present in an amount of 13%, threonine is present in an amount of 27%, lysine is present in an amount of 19%, and the percent calculated based upon the total amino acid content, by weight, in the food supplement;

the mineral content comprises 500 µg of chromium picolinate per dose of the food supplement.

8. The method of claim 7, wherein the dose of the food supplement is administered as the subject consumes a meal.

* * * * *